(12) United States Patent
Wix

(10) Patent No.: US 9,346,725 B2
(45) Date of Patent: May 24, 2016

(54) PROCESS FOR THE PREPARATION OF HIGHER ALCOHOLS

(71) Applicant: Haldor Topsøe A/S, Kgs. Lyngby (DK)

(72) Inventor: Christian Wix, Nærum (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 14/358,377

(22) PCT Filed: Nov. 7, 2012

(86) PCT No.: PCT/EP2012/072022
§ 371 (c)(1),
(2) Date: May 15, 2014

(87) PCT Pub. No.: WO2013/072230
PCT Pub. Date: May 23, 2013

(65) Prior Publication Data
US 2014/0330050 A1  Nov. 6, 2014

(30) Foreign Application Priority Data

Nov. 18, 2011  (DK) .................................. 2011 00904

(51) Int. Cl.
*C07C 29/34* (2006.01)
*C07C 29/32* (2006.01)
*C07C 29/151* (2006.01)
*C07C 29/132* (2006.01)
*C07C 29/76* (2006.01)

(52) U.S. Cl.
CPC ............... *C07C 29/34* (2013.01); *C07C 29/132* (2013.01); *C07C 29/1518* (2013.01); *C07C 29/32* (2013.01); *C07C 29/76* (2013.01)

(58) Field of Classification Search
None
See application file for complete search history.

(56) References Cited

U.S. PATENT DOCUMENTS

| 2,468,510 | A | * | 4/1949 | Owen | ............................ 518/705 |
| 4,752,622 | A |  | 6/1988 | Stevens | |
| 2011/0046421 | A1 | * | 2/2011 | Daniel et al. | ................... 568/885 |

FOREIGN PATENT DOCUMENTS

| CN | 101535217 A | 9/2009 |
| EP | 0 048 980 A1 | 4/1982 |
| WO | WO 2008/048364 A2 | 4/2008 |

OTHER PUBLICATIONS

Kevin J. Smith et al., "A Chain Growth Scheme for the High Alcohols Synthesis," Journal of Catalysis, 1984, vol. 85, pp. 428-436.

* cited by examiner

Primary Examiner — Yong Chu
Assistant Examiner — Ana Z Muresan
(74) Attorney, Agent, or Firm — Blank Rome LLP

(57) ABSTRACT

Process for production of a higher alcohol product from an alcohol synthesis gas comprising hydrogen, carbon monoxide, carbon dioxide, and lower alcohols, comprising a carbon dioxide and optional alkane removal step. Use a stripper using synthesis gas as stripping gas to purify the liquid phase containing the lower and highers alcohols, in order to strip the lower alcohol from the alcohol stream. Synthesis gas used for stripping is used as recycle stream in the reactor.

14 Claims, 1 Drawing Sheet

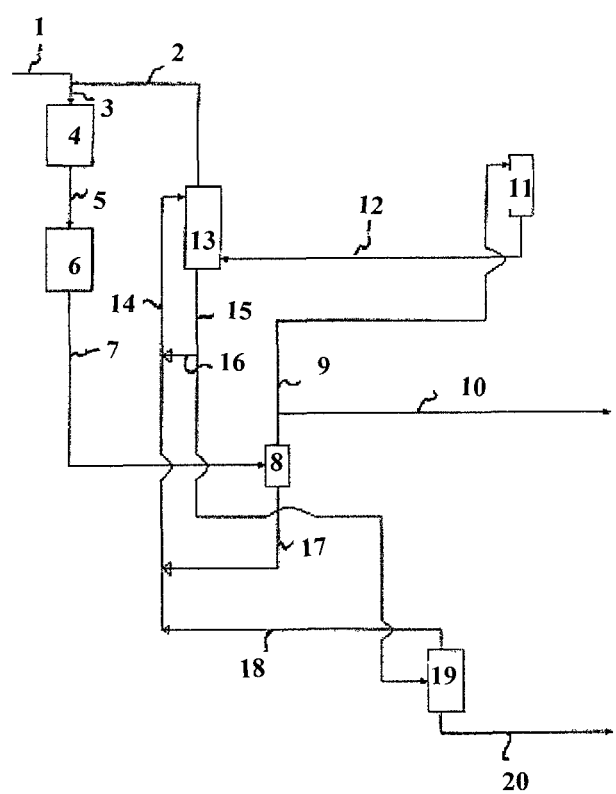

PROCESS FOR THE PREPARATION OF HIGHER ALCOHOLS

BACKGROUND OF THE INVENTION

1. Field of the Invention

The present invention relates to the production of higher alcohols. In particular the invention is a process for the preparation of these alcohols by conversion of carbon monoxide and hydrogen containing synthesis gas admixed with lower alcohols in presence of one or more catalysts being active in the conversion of carbon monoxide and hydrogen to higher alcohols.

2. Description of the Related Art

It is known that higher alcohols and other oxygenates are formed as by-product in the catalytic methanol synthesis from synthesis gas.

It is also known that higher alcohol products can be produced directly from synthesis gas.

US patent application No. 2009/0018371 discloses a method for the producing alcohols from synthesis gas. The synthesis gas is in a first step partially converted to methanol in presence of a first catalyst and in a second step methanol is converted with a second amount of synthesis gas to a product comprising C2-C4 alcohols in presence of a second catalyst. The second amount of synthesis gas can include unreacted synthesis gas from the first step.

The alcohol synthesis requires a high concentration of carbon monoxide in the synthesis gas. A useful synthesis gas has a $H_2/CO$ ratio of at least 0.4. The synthesis gas for the higher alcohol synthesis is prepared by the well-known steam reforming process of liquid or gaseous hydrocarbons or by means of gasification carbonaceous material, like coal, heavy oil, petroleum coke and bio mass.

Hydrogen and carbon monoxide react to produce methanol:

Syngas to methanol,

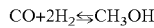

The methanol reacts with the syngas and a chain growth to higher alcohols is initiated, according to the following reaction scheme:

Chain growth by reaction with synthesis gas,

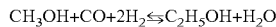

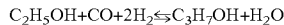

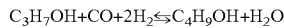

etc.

It has been found that addition of lower alcohols to the synthesis gas results in a drastic increase in the yield of higher alcohols when compared to the conventional methanol synthesis gas.

As used hereinbefore and in the following description and the claims, the term "lower alcohols" refers to alcohols present in synthesis gas for use in the higher alcohol synthesis and the term "higher alcohols" refers to alcohols higher than the alcohols in the alcohol synthesis gas.

The alcohols obviously couple together and form higher alcohols:

Aldol coupling,

etc.

SUMMARY OF THE INVENTION

Pursuant to the above findings and observations, the general embodiment of this invention is a process for production of a higher alcohol product, comprising the steps of (a) providing an alcohol synthesis gas comprising hydrogen, carbon monoxide and lower alcohols by mixing a fresh synthesis gas with a gaseous recycle stream comprising the lower alcohols;

(b) converting the alcohol synthesis gas into a crude alcohol product stream comprising higher alcohols and unconverted alcohol synthesis gas in presence of one or more catalysts active in conversion the alcohol synthesis gas;

(c) cooling and separating the crude alcohol product stream withdrawn from step (b) into a gas phase comprising hydrogen, carbon monoxide and carbon dioxide and optionally alkanes and into a liquid product comprising the lower alcohols from the unconverted alcohol synthesis gas and the higher alcohols formed in the conversion of the alcohol synthesis gas;

(d) subjecting the gas phase from step (c) to a carbon dioxide and optional alkane removal step and reducing content of carbon dioxide and optionally alkanes in the gas phase;

(e) recycling the liquid product obtained from step (c) to a stripping treatment and stripping the liquid product with the gas phase obtained in step (d) to form the recycle stream in step (a);

(f) subsequent the stripping treatment of the liquid phase in step (e) withdrawing the stripped liquid phase being depleted in the lower alcohols and subjecting the thus treated liquid phase to a separation; and (g) recovering the higher alcohol product from the separation in step (f).

Fresh synthesis gas to be admixed with the recycle stream may be generated by steam reforming of hydrocarbons or gasification of a carbon-based feedstock. The $H_2/CO$ ratio may be adjusted by conventional membrane technology, sweet and/or sour shift reaction or other means known in the art. Sulphur (if any) is removed in a sulphur guard or by a chemical or physical wash known in the art.

Catalysts being active in the conversion of synthesis gas to higher alcohols are per se known in the art, e.g. from U.S. Pat. No. 5,096,688, U.S. Pat. No. 4,956,392, U.S. Pat. No. 4,675,343 and U.S. Pat. No. 4,943,551. For use in the present invention a preferred catalyst consists of copper, zinc oxide and aluminium oxide, optionally promoted with one or more metals selected from alkali metals, basic oxides of earth alkali metals and lanthanides.

The alcohol synthesis can be performed in an adiabatic operated reactor with quench cooling, a gas cooled reactor or preferably in a cooled boiling water reactor, producing high pressure steam. In the boiling water reactor large di-ameter tubes may be used due to the modest reaction rate.

The synthesis of higher alcohols is preferably carried out at a pressure of at least 2 MPa, typically between 2 and 15 MPa and a temperature above 220° C., preferably between 270 and 400° C.

As mentioned hereinbefore, alcohols like methanol, ethanol and propanol participate in the synthesis of higher alcohol resulting in a large increase of the rate of formation of higher alcohols.

It has proven that that increased concentrations of lower alcohols in the alcohol synthesis gas results in an increased yield of higher alcohols.

Thus, in a specific embodiment of the invention, the lower and higher alcohol containing liquid phase obtained in step (c) is admixed with a stream of lower alcohols being separated from the higher alcohol product in the separation step (f) before being introduced into the stripping treatment or during the stripping treatment in step (e).

Thereby, a higher concentration of lower alcohols can be stripped off from the liquid phase into the washed gaseous phase, which then is introduced into the alcohol synthesis gas via the recycle stream from the stripping treatment.

In still an embodiment of the invention, the production of higher alcohols is boosted by addition of a stream of lower alcohols from an externals source into the alcohol synthesis gas upstream the conversion in step (b), such as a stream of bioethanol or crude methanol product and the like.

In the synthesis of alcohols, minor amounts of alkanes by-products are formed by hydrogenation:

$$H_2 + CH_3OH \leftrightarrows CH_4 + H_2O$$

$$H_2 + C_2H_5OH \leftrightarrows C_2H_6 + H_2O$$

etc.

Carbon dioxide is formed in the synthesis by the water-gas-shift reaction:

$$CO + H_2O \leftrightarrows CO_2 + H_2$$

Alkanes behave inert in the alcohol synthesis and carbon dioxide as an inhibitor and should be removed continuously to prevent these gases from accumulating in the synthesis loop.

It has proven that a physical wash with e.g. methanol reduces both the content of carbon dioxide and alkanes.

Thus, in a further embodiment of the invention, amounts of alkane by-products are reduced together with carbon dioxide by means of a physical wash in step (d), including a methanol wash.

As already mentioned above, in the synthesis of higher alcohols small amounts of aldehydes, ketons and esters together with other oxygenates are formed as by-products. These by-products may form azeotropic mixtures with the higher alcohols or have boiling points close to the alcohols and leave the purification of the product difficult.

In a specific embodiment of the invention, the crude alcohol product being withdrawn from the alcohol synthesis step (b) is subjected to a hydrogenation step in presence of a hydrogenation catalyst, wherein the oxygenate by-products are hydrogenated to their corresponding alcohols. Thereby, the final distillation of the product is much improved.

For the purpose of the product hydrogenation, the crude alcohol product is cooled in a feed effluent heat exchanger to a temperature between 100 and 200° C. and introduced into a hydrogenation reactor containing a bed of hydrogenation catalyst. Useful hydrogenation catalysts are catalysts containing noble metals including platinum and palladium or a copper/zinc oxide/alumina catalyst being also employed in the alcohol synthesis.

In case the process is performed with the above hydrogenation step, the alcohol synthesis gas can further be admixed with ketones and/or aldehydes from an external source. These compounds are then hydrogenated in the hydrogenation step to their corresponding alcohols, which further boosts the production yield of higher alcohols.

The ketones and/or aldehydes are advantageously introduced into the synthesis gas by means of the recycle stream by admixing the stream of ketones and/or aldehydes during the stripping of the liquid phase in step (e).

When using an oxidic alcohol formation catalyst together with a synthesis gas with a high content of carbon monoxide, the catalyst has a reduced operation time. The catalyst bed will after a time on stream be clogged with waxy material and has to be removed.

This problem arises during preparation of the synthesis gas under conditions to provide a relatively high content of carbon monoxide. Carbon monoxide reacts with the steel equipment used in the synthesis gas preparation and forms i.e. iron carbonyl compounds. When transferred to the alcohol synthesis catalyst, these compounds catalyse the Fischer-Tropsch reaction and the waxy material is formed on the catalyst.

By removing the carbonyl compounds from the synthesis gas upstream of the alcohol synthesis, the operation time of the catalyst can be much improved.

A particular useful metal carbonyl sorbent for use in the inventive process comprises copper aluminium spinel being modified by calcination at elevated temperature in an oxidizing atmosphere followed by a reduction in a reducing atmosphere, such as synthesis gas or synthesis gas diluted with an inert gas, prior to being contacted with metal carbonyl contaminated synthesis gas.

Copper aluminum spinels are per se known compounds and the preparation of copper aluminum spinel is described in the art e.g. Z. Phys. Chem., 141 (1984), 101-103.

Preferably, the particulate sorbent further comprises copper oxide in excess to the amount being present in the copper aluminum spinel prior to modification.

A typical preparation method comprises co-precipitation of copper and aluminum salts and calcination in air at a temperature of between 700° C. and 900° C. to form crystals with the spinel structure.

These sorbents remove carbonyl compounds from the synthesis gas to the low ppb range, preferably below 1 ppb.

The sorbent may be arranged as an isothermal guard reactor in front of the alcohol synthesis reactor or as top layer on a fixed catalyst with the one or more catalysts catalysing the conversion of the synthesis gas.

The absorber is effective at inlet temperature of the alcohol synthesis gas mixture of between 200 to 250° C. Therefore it is preferred to place the absorbent directly on top of the alcohol preparation catalyst bed instead of having a separate absorber reactor, which would also imply a cooling and/or heating step of the synthesis gas prior to introduction into the alcohol reactor.

As already mentioned above, the process product, i.e. the crude higher alcohol product is cooled in order to condensate the alcohols. The vapour and liquid phase are separated in a separator. A part of the process gas is then purged in order to reduce the amount of inerts accumulating in the loop (e.g. Ar, $N_2$, alkanes).

The gas phase is treated in a methanol wash system to remove the majority of $CO_2$ and at least a part the amounts of alkanes in the recycle gas, but also alkanes.

BRIEF DESCRIPTION OF THE DRAWINGS

The invention is described in more detail in the following description with reference to the drawings, in which FIG. 1 is a simplified flow sheet of a process for the preparation of higher hydrocarbons according to a specific embodiment.

DETAILED DESCRIPTION OF THE PREFERRED EMBODIMENTS

Referring to FIG. 1, alcohol synthesis gas 3 is formed by mixing fresh synthesis gas 1 with recycle gas 2.

The thus formed synthesis gas 3 is introduced into higher alcohol synthesis reactor 4.

The crude alcohol product 5 from the synthesis reactor 4 contains higher alcohols, methanol, ethanol, propanol traces of water and traces of reaction by-products, i.e. alkanes, ketones, aldehydes, methyl acetate and methyl formate. Furthermore, it contains gaseous compounds including hydrogen, carbon monoxide, carbon dioxide, nitrogen and argon from the raw syngas.

For the removal or reduction of the amounts of aldehydes, ketons and esters together with other oxygenates the crude alcohol product 5 is cooled (not shown) and passed into hydrogenation reactor 6. These compounds are hydrogenated with hydrogen contained in the unconverted synthesis gas from reactor 4 in presence of a hydrogenation catalyst.

The hydrogenated crude alcohol product 7 is cooled (not shown). The cooled product is the separated in separator 8 into vapour and liquid phase, 9 and 17, respectively. A part of gas phase 9 is then purged through line 10 to reduce the amount of inerts accumulating in the synthesis loop (e.g. Ar, $N_2$, alkanes).

The remainder of the gas phase is treated in a methanol wash system 11 to remove the majority of $CO_2$ in the gas phase gas and alkanes.

After $CO_2$ and alkane removal the gas phase is passed in line 12 to stripper 13.

Stripper 13 is operated in such manner that the less volatile higher alcohols leave the stripper as bottom product together with residual amounts of lower alcohols having not been stripped off into the recycle gas. The major amount of the lower alcohols leaves the stripper as overhead together with gaseous phase and forms recycle stream 2.

Liquid stream 14 being stripped with the washed gaseous phase from line 12 is a mixture of three separated streams preheated in a heater (not shown). A first of these streams is a split fraction 16 of stripper liquid effluent 15. The remainder of liquid effluent 15 is passed to distillation section 19. A second stream is liquid phase 17 from separator 8 and a third is the overhead fraction 18 from distillation section 19 with lower alcohols separated from higher alcohols in the distillation section.

The less volatile higher alcohols leave the distillation section with the bottom product.

The invention claimed is:

1. A process for production of a higher alcohol product, comprising the steps of:
    (a) providing an alcohol synthesis gas comprising hydrogen, carbon monoxide and lower alcohols by mixing a fresh synthesis gas with a gaseous recycle stream comprising the lower alcohols;
    (b) converting the alcohol synthesis gas into a crude alcohol product stream comprising higher alcohols and unconverted alcohol synthesis gas in presence of one or more catalysts active in conversion the alcohol synthesis gas;
    (c) cooling and separating the crude alcohol product stream withdrawn from step (b) into a gas phase comprising hydrogen, carbon monoxide and carbon dioxide and optionally alkanes and into a liquid product comprising the lower alcohols from the unconverted alcohol synthesis gas and the higher alcohols formed in the conversion of the alcohol synthesis gas;
    (d) subjecting the gas phase from step (c) to a carbon dioxide and optional alkane removal step and reducing content of carbon dioxide and optionally alkanes in the gas phase;
    (e) recycling the liquid product obtained from step (c) to a stripping treatment and stripping the liquid product with the gas phase obtained in step (d) to form the recycle stream in step (a);
    (f) subsequent the stripping treatment of the liquid phase in step (e) withdrawing the stripped liquid phase being depleted in the lower alcohols and subjecting the thus treated liquid phase to a separation; and
    (g) recovering the higher alcohol product from the separation in step (f).

2. The process of claim 1, wherein the one or more catalysts in step (b) comprise copper, zinc oxide and aluminium oxide and are optionally promoted with one or more metals selected from alkali metals, basic oxides of earth alkali metals and lanthanides.

3. The process of claim 1, comprising the further step of introducing a stream of the lower alcohols being separated from the higher alcohol product in the separation of step (f) into the stripping treatment of step (e).

4. The process of claim 1, comprising the further steps of:
    cooling the crude alcohol product from step (b); and
    contacting the cooled product with a hydrogenation catalyst in presence of a hydrogenation catalyst prior to introduction into step (c).

5. The process of claim 1, wherein amounts of carbonyl compounds being present in the alcohol synthesis gas are reduced in the synthesis gas by contacting the gas with a sorbent comprising copper aluminium spinel being modified by reduction in a reducing atmosphere at a temperature of between 200° C. and 500° C. prior to being contacted with the synthesis gas.

6. The process of claim 5, wherein the sorbent comprises copper in excess to the amount of copper contained in the copper aluminum spinel.

7. The process of claim 5, wherein the sorbent is arranged on top of a fixed bed of catalyst in step (b).

8. The process of claim 1, wherein the conversion of the alcohol synthesis gas is performed at a pressure of between 2 and 15 MPa and a temperature of above 220° C.

9. The process of claim 4, wherein the hydrogenation catalyst comprises copper, zinc oxide and aluminium oxide.

10. The process of claim 4, wherein the hydrogenation catalyst comprises platinum and/or palladium.

11. The process of claim 1, wherein a further stream of lower alcohols is introduced into the alcohol synthesis gas upstream the step (b).

12. The process of claim 4, wherein a further stream of ketones and/or aldehydes is introduced into the alcohol synthesis gas.

13. The process of claim 12, wherein the further stream of ketones and/or aldehydes is introduced during the stripping treatment in step (e).

14. The process of claim 1, wherein the carbon dioxide and alkane removal step is performed by a physical wash.

* * * * *